United States Patent [19]

Carlos

[11] 4,370,218

[45] Jan. 25, 1983

[54] INORGANIC SALT OXIDATION PROMOTERS FOR HYDROCARBONS

[75] Inventor: Donald D. Carlos, Louisville, Ky.

[73] Assignee: Ashland Petroleum Company, division of Ashland Oil, Inc., Ashland, Ky.

[21] Appl. No.: 245,801

[22] Filed: Mar. 20, 1981

[51] Int. Cl.³ .................. C07C 27/10; C07C 27/12; C10G 3/00
[52] U.S. Cl. .................................. 208/3; 208/5
[58] Field of Search .............................. 208/5, 6, 3

[56] References Cited

U.S. PATENT DOCUMENTS

| | | | |
|---|---|---|---|
| 1,997,569 | 4/1935 | Craig et al. | 208/5 |
| 2,410,642 | 11/1946 | Farkas et al. | 260/593 |
| 2,424,671 | 7/1947 | Stossel | 196/142 |
| 2,472,152 | 6/1949 | Farkas et al. | 44/57 |
| 2,861,936 | 11/1958 | Birikauer et al. | 208/6 |
| 2,886,506 | 5/1959 | Brown et al. | |

FOREIGN PATENT DOCUMENTS

| | | | |
|---|---|---|---|
| 47-17314 | 2/1972 | Japan | 208/6 |
| 26426 | of 1913 | United Kingdom | 208/6 |

*Primary Examiner*—Delbert E. Gantz
*Assistant Examiner*—Helane E. Maull
*Attorney, Agent, or Firm*—Sughrue, Mion, Zinn, Macpeak & Seas

[57] ABSTRACT

Liquid hydrocarbons are oxidized in the presence of an inorganic salt promoter.

18 Claims, No Drawings

INORGANIC SALT OXIDATION PROMOTERS FOR HYDROCARBONS

BACKGROUND OF THE INVENTION

The present invention relates to the oxidation of hydrocarbons. More specifically, the present invention relates to the oxidation of hydrocarbon waxes and petrolatums. Oxidized petroleum fractions including waxes and petrolatums have, in the past, been employed as the source of saponifiable material in the production of lubricating greases and in the formulation of protective coatings. The oxidates employed for these purposes have been obtained by oxidizing selected petroleum fractions under controlled conditions such that the oxidation proceeds only to a limited extent.

Oxidation of petroleum fractions by the above-described method had, associated with it, certain difficulties. Some petroleum fractions are not easily oxidized by the prior art processes and even though oxidizable, in some instances, require a preliminary induction period before the rate of oxidation becomes appreciable. Another problem associated with oxidizing petrolatums is the discoloration of the final wax product rendering it aesthetically unattractive for use in some formulations.

Other problems involve the presence of various oxidation inhibitors in the hydrocarbon fraction. These oxidation inhibitors are often nitrogen and/or sulfur-containing compounds present as impurities in the hydrocarbon source.

To overcome the above problems, the prior art suggests the employment of various oxidation catalysts, such as redox catalysts with or without promoters, for use in the hydrocarbon oxidation process. The redox catalysts are often based on expensive redox metals, such as manganese, chromium and the like.

U.S. Pat. No. 2,410,642 to Farkas et al. discloses the partial oxidation of either a narrow boiling point low molecular weight hydrocarbon fraction or a single hydrocarbon to prepare predominantly alcohols and ketones. As catalysts, this reference teaches the use of metals of atomic number 20 to 30, that is, redox metal catalysts. Calcium, scandium, titanium, vanadium, chromium, manganese, iron, cobalt, nickel, copper, zinc, magnesium, aluminum, molybdenum, silver, tin, tantalum and uranium metals are recited, which can be provided by the free metal or metallic salts such as the metal nitrates, sulfates, sulfites, phosphates, phosphites, etc. The narrow hydrocarbon range and single hydrocarbon feeds contemplated by Farkas et al are those which are oxidizable in the absence of the metal catalyst.

U.S. Pat. No. 2,424,671 to Staussel discloses the reaction of oxygen compounds of chlorine with mercaptans in tank bottoms to convert the mercaptans to oxygen promoters, prior to an air oxidation step.

U.S. Pat. No. 2,472,152 to Farkas et al. discloses the partial oxidation of diesel engine fuel with oxidizing agents such as aqueous solutions of oxyhalogen acids.

SUMMARY OF THE INVENTION

An object of this invention is to provide an improved process for the oxidation of hydrocarbon waxes and petrolatums using an oxidizing gas.

Another object of this invention is to provide a process for oxidizing hydrocarbon waxes and petrolatums more easily than has heretofore been possible.

A further object of this invention is to provide a process for oxidizing hydrocarbon fractions containing redox metal catalyst poisoners.

Still another object of this invention is to provide improved hydrocarbon oxidates characterized by superior color and reduced odor, without the need of expensive metal redox catalysts.

Another object of this invention is to provide an improved process for the oxidation of hydrocarbons not requiring an induction period while providing a controlled rate of oxidation to oxidates of high acid number.

Other objects of this invention will be apparent to the skilled artisan.

In accordance with the present invention, the oxidation of hydrocarbons is carried out by blowing an oxidizing gas through a liquid or molten mass of hydrocarbons in the presence of an oxidation promoting amount of an inorganic salt, the anion of which is based on a phosphorous atom, a sulfur atom, a nitrogen atom, a silicon atom or a halogen atom.

More specifically, in the present invention, an oxidation promoting amount of an inorganic phosphate, phosphite, sulfate, sulfite, halate, halite, silicate, nitrate or nitrite is used to promote gaseous oxidation of liquid or molten hydrocarbons. In preferred embodiments, the cationic portion of the inorganic salt is provided by one or more monovalent ions.

In preferred embodiments of the present invention, the inorganic salt oxidation promoter is present in an amount of about 0.05 to 2.0 parts by weight per 100 parts of hydrocarbon feed having an average number of hydrocarbons per molecule of 20 to 100.

The oxidation is conducted under suitable conditions of gas flow, pressure and temperature to oxidize the hydrocarbon wax or petrolatum to a predetermined acid number.

DETAILED DESCRIPTION OF THE INVENTION

As disclosed above, in the present invention the important characteristic of the inorganic salt is the anion, which is an anion based on a phosphorous atom, a nitrogen atom, a sulfur atom, a silicon atom or a halogen atom. This means that the only other atoms which can be present in the anion are oxygen atoms. The cation of the salt promoter will most usually be an alkali metal ion, an alkaline earth metal ion or the ammonium ion. With the exception of the sulfates and sulfites, the various "hypo" salts are also contemplated.

The phosphorous-containing inorganic salts usable in the present invention include the mon-, di- and tri- basic phosphates, phosphites and hypophosphites. With "M" representing a suitable cation, these compounds can be represented by the following formulae:

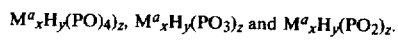

$M^a{}_xH_y(PO_4)_z$, $M^a{}_xH_y(PO_3)_z$ and $M^a{}_xH_y(PO_2)_z$.

In all of the above formulae, a is the valence of M and is 1, 2 or 3, and y must be 0 when a is 2 or 3. When a is 1, x is $3-y$ and z is 1; when a is 2, x is 3 and z is 2; when a is 3, x and z are both 1. For example, when a is 1, the following possibilities exist: $M_3PO_4$, $M_2HPO_4$, $MH_2PO_4$, $M_3PO_3$, $M_2HPO_3$, $MH_2PO_3$, $M_3PO_2$, $M_2HPO_2$ and $MH_2PO_2$. Preferably, M is an alkali metal ion, an alkaline earth metal ion or the ammonium ion.

Some specific examples of the above-type of promoter compound usable in the present invention are Na$_3$PO$_4$.12H$_2$O, K$_3$PO$_4$, Ca$_3$(PO$_4$)$_2$, (NH$_4$)$_2$HPO$_4$, Na$_3$PO$_3$, Na$_2$HPO$_3$.5H$_2$O and NaH$_2$PO$_2$.H$_2$O.

The sulfur-containing salts usable in the present invention include the sulfates and sulfites. With M representing a suitable cation, these compounds can be represented by the following formulae:

$$M^a{}_x(SO_4)_y \text{ and } M^a{}_x(SO_3)_y.$$

In each of the above formulae, a is the valence of M and is 1, 2 or 3. When a is 1, x is 2 and y is also 1; when a is 2, both x and y are 1; and when a is 3, x=2 and y is 3. Preferably, M is an alkali metal ion, an alkaline earth metal ion or the ammonium ion.

Some specific examples of the above-type of promoter compound usable in the present invention are Na$_2$SO$_4$, CaSO$_4$, K$_2$SO$_4$, (NH$_4$)$_2$SO$_4$, Na$_2$SO$_3$ and K$_2$SO$_3$.

The halogen-containing salts usable in the present invention include the halates, halites, hypohalites and perhalates. With M representing a suitable cation, and X representing a halogen ion selected from Cl, Br and I these compounds can be represented by the following formulae:

$$M^a{}_x(XO_3)_y, M^a{}_x(XO_2)_y, M^a{}_x(XO)_y \text{ and } M^a{}_x(XO_4)_y.$$

In each of the above formulae, a is the valence of M and is 1, 2 or 3, x is always 1 and y is the same integer as a. Preferably, M is an alkali metal ion, an alkaline earth metal ion or the ammonium ion. Most preferably X is Cl.

Some specific examples of the above-type of promoter compound usable in the present invention are KBrO$_3$, NaClO.H$_2$O, Ca(ClO)$_2$, NaClO$_3$, KClO, NaClO$_4$ and NaClO$_2$.

The silicon-containing salts usable in the present invention include the various water-soluble salts of the silicic acids, that is, both the orthosilicates (—SiO$_4{}^{-4}$) and the metasilicates (—SiO$_3{}^{-2}$) and even the disilicates and trisilicates such as sodium disilicate. Waterglass is a preferred silicate salt, and may be represented by the formula (Na$_2$O).x SiO$_2$, wherein x is 3 to 5. Other preferred compounds are sodium metasilicate and sodium orthosilicate. As long as the compound has reasonable water solubility, salts of the following silicic acids are usable, where at least one hydrogen atom has been replaced by a metallic ion or ammonium ion. The valency of the cation can be 1, 2 or 3, with, of course, in all cases the number of cations and anions being that to provide a stable salt-type compound:

H$_2$Si$_4$O$_9$, H$_2$Si$_2$O$_5$, H$_4$SiO$_3$O$_8$, H$_2$SiO$_3$, H$_8$Si$_3$O$_{10}$, H$_6$Si$_2$O$_7$ and H$_4$SiO$_4$.

Again, the preferred cations are the alkali metal ions, the alkaline earth metal ions and the ammonium ion, with sodium ion being most preferred.

The nitrogen-containing salts usable in the present invention include the nitrates and nitrites. With M representing a suitable cation, these compounds can be represented by the formulae:

$$M^a{}_x(NO_3)_y \text{ and } M^a{}_x(NO_2)_y$$

wherein a is the valence of M and is 1, 2 or 3. y is the same integer as a, while x is always the integer 1.

Some specific examples of the above-type of promoter compound usable in the present invention are KNO$_3$, NaNO$_2$, Ca(NO$_3$)$_2$, NaNO$_3$, NH$_4$NO$_3$, KNO$_2$ and NH$_4$NO$_2$.

Again, M is preferably an alkali metal ion, an alkaline earth metal ion or the ammonium ion.

Generally, the promoter compound will be added to the hydrocarbon feed in the form of an aqueous solution since it is preferred to have a small amount of water, say about up to 4 parts by weight per 100 parts of hydrocarbon feed, present during the oxidation. The promoter compound is preferably present in 0.1 to 1.0 parts per 100 parts of hydrocarbon feed.

The hydrocarbons useful in this process include the conventional feedstocks used as oxidizer feedstock. Ordinarily, such a feedstock comprises a mixture of saturated hydrocarbons having an average number of carbon atoms per molecule of 20 to 100, preferably 25 to 50. Waxes and petrolatums from crude oil refining, hydrocarbon mixtures from lubricant plants and the like are examples of suitable feedstocks.

Ordinarily, the process will be carried out as a batch process. Air or an other oxidizing gas is forced through the reaction mixture of hydrocarbon and promoter compound at a rate of between 0.5 and 10 liters, preferably 3.5 to 4.0 liters (measured at 760 mm of mercury and 24° C.) per liter of hydrocarbon per minute at a temperature of between 150° and 180° C., preferably 160° to 165° C. Ordinarily, the temperature will rise as the oxidation proceeds so that only minimal heat may be required for the oxidation. The oxidation process is conducted at a pressure of between 50 and 400 psig (4.4–28.2 atmospheres), preferably 150 to 250 psig. The process is discontinued when a desired acid number is reached. The term "acid number" is defined to mean the number of milligrams of potassium hydroxide required to neutralize 1 gram of sample. Generally, the reaction will be carried out for about 0.25 to 10 hours, preferably about 1 to 5 hours to reach a predetermined acid number.

EXAMPLE 1

A number of air oxidations were conducted in laboratory tests using a one liter Parr bomb. In each test, the reactor charge mounted to approximately 500 cc of hydrocarbon. To the hydrocarbon material there was added the amount of inorganic promoter compound as shown in the accompanying table. For comparison purposes, some runs were carried out in the absence of the inorganic promoter compound. Unless otherwise indicated, the reaction conditions were approximately 1 hour or 3 hours for each reaction at a temperature of approximately 320° to 330° F., a pressure of 200 psig and an air input rate of 1.9 liters of air per minute (measured at 25° C. and one atmosphere). Acid number determinations were made at the end of each run.

TABLE 1

Batch Air Oxidation of Hydrocarbons With and Without Addition of Inorganic Promoter Compound

| Run No. | Hydrocarbon Type | Percentage by Weight Inorganic Compound Added | Reaction Time | Acid Number |
|---|---|---|---|---|
| 1-A | (1) | 0.5% KBrO$_3$ in 10 cc water | 1 hour | 9.8 |
| 1-B | (1) | 0.5% K$_3$PO$_4$ in 10 cc water | 1 hour | 11.0 |
| 1-C | (1) | None | 3 hours | 0.4 |
| 1-D | (1) | 0.5% KNO$_3$ in 10 cc water | 1 hour | 10.0 |
| 1-E | (1) | 0.5% Na$_2$SiO$_3$.5H$_2$O 0.5% NaH$_2$PO$_4$.H$_2$O | 3 hours | 45.5 |

TABLE 1-continued

Batch Air Oxidation of Hydrocarbons With and Without Addition of Inorganic Promoter Compound

| Run No. | Hydro-carbon Type | Percentage by Weight Inorganic Compound Added | Reaction Time | Acid Number |
|---|---|---|---|---|
| 2-A | (2) | in 5 cc water 0.5% Na₃PO₄.12H₂O | 3 hours | 44.3 |
| 2-B | (2) | in 10 cc water 0.24% NaNO₂ | 3 hours | 42.0 |
| 2-C | (2) | in 5 cc water 0.5% Ca(NO₃)₂ | 3 hours | 45.0 |
| 2-D | (2) | in 5 cc water 0.25% NaClO.H₂O | 3 hours | 42.4 |
| 2-E | (2) | in 5 cc water 0.25% (NH₄)₂HPO₄ | 3 hours | 39.7 |
| 3-A | (3) | in 5 cc water | 1 hour | 12.3 |
| 3-B | (3) | None | 3 hours | 0.7 |
| | | 0.5% Na₂SO₄ | | |
| 3-C | (3) | in 10 cc water 0.5% K₂SO₄ | 3 hours | 46.0 |
| 3-D | (3) | in 10 cc water 0.5% water | 3 hours | 48.0 |
| 3-E | (3) | glass solution | 1 hour | 14.3 |
| 4-A | (4) | None | 3 hours | 2.35 |
| | | 0.5% (NH₄)₂SO₄ | | |
| 4-B | (4) | in 10 cc water 0.25% CaSO₄ | 3 hours | 52.0 |
| 4-C | (4) | in 15 cc water | 3 hours | 51.1 |
| 5-A | (5) | None | 3 hours | 1.6 |
| | | 0.5% NaSO₄ | | |
| 5-B | (5) | in 10 cc water 0.5% Ca(ClO)₂ | 3 hours | 47.0 |
| 5-C | (5) | in 10 cc water 0.5% Na₂SO₃ | 3 hours | 37.1 |
| 6-A | (6) | in 10 cc water | 3 hours | 47.7 |

(1) 330 neutral wax from a lube plant.
(2) 100 neutral wax from a mixture of Iranian Rostam and Louisiana sweet crude.
(3) 100 neutral wax from a lube plant.
(4) 100 neutral wax from Iranian Rostam crude.
(5) 250 neutral wax from Iranian Rostam crude.
(6) 250 neutral wax from Murban.

Variations of the invention will be apparent to the skilled artisan.

What is claimed is:

1. A process for oxidizing liquid saturated hydrocarbons primarily containing petrolatums and waxes, said hydrocarbons containing an average of about 20 to about 100 carbon atoms per molecule comprising blowing an oxidizing gas through a liquid mass of said hydrocarbons under a pressure of about 50 to 400 psia in the presence of an oxidation promoting amount of an inorganic salt, the anion of which consists of one or more phosphorous, nitrogen, sulfur, silicon or halogen atoms and one or more oxygen atoms to yield an oxidized hydrocarbon product having an acid number of at least 9.8.

2. The process of claim 1 wherein said inorganic salt is a phosphate, a phosphite, a sulfate, a sulfite, a halate, a halite, a silicate, a nitrate or a nitrite.

3. The process of claim 2 wherein the cation of said inorganic salt is an alkali metal ion, an alkaline earth metal ion or the ammonium ion.

4. The process of claim 1, 2 or 3 wherein said inorganic salt is present in an amount of 0.1 to 1.0 parts per 100 parts of hydrocarbons, by weight.

5. The process of claim 1, 2 or 3 wherein said inorganic salt is present in an amount of 0.05 to 2.0 parts per 100 parts of hydrocarbons, by weight, sid hydrocarbons are a mixture of saturated hydrocarbons having an average number of carbon atoms per molecule of 20 to 100 and the salt is added admixed with a small amount of water.

6. The process of claim 1, 2 or 3 wherein said inorganic salt is present in an amount of 0.05 to 2.0 parts per 100 parts of hydrocarbons, by weight, said hydrocarbons are a mixture of saturated hydrocarbons having an average number of carbon atoms per molecule of 20 to 100 and the salt is added admixed with a small amount of water, and wherein air is the oxidizing gas and is blown through the hydrocarbons at a rate of about 0.5 to 10 liters (measured at 760 mm mercury and 25° C.) per liter of hydrocarbons per minute while the reaction is being carried out at about 150° C. to 180° C. under a pressure of about 50 to 400 psig for about 0.25 to 10 hours.

7. The process of claim 6 wherein the amount of inorganic salt is about 0.1 to 1.0 parts per 100 parts of hydrocarbons, by weight, said hydrocarbons having an average number of carbon atoms of 25 to 50, the air is blown at a rate of 3.5 to 4.0 liters per minute per liter of hydrocarbons, the temperature of reaction is 160° C. to 165° C., the pressure is 150 to 250 psig and the reaction is carried out for about 1 to 5 hours.

8. The process of claim 4 wherein said inorganic salt is represented by one of the following formulae:

$M^a{}_xH_y(PO_4)_z$, $M^a{}_xH_y(PO_3)_z$ and $M^a{}_xH_y(PO_2)_z$, wherein m is a cation, a is the valence of M and is 1, 2 or 3, and y must be 0 when a is 2 or 3, when a is 1, x is 3−y and z is 1; when a is 2, x is 3 and z is 2; when a is 3, x and z are both 1.

9. The process of claim 8 wherein said inorganic salt is Na₃PO₄.12H₂O, K₃PO₄, Ca₃(PO₄)₂, (NH₄)₂HPO₄, Na₃PO₃, Na₂HPO₃.5H₂O or NaH₂PO₂.H₂O.

10. The process of claim 4 wherein said inorganic salt is represented by one of the following formulae:

$M^a{}_x(SO_4)_y$ and $M^a{}_x(SO_3)_y$ wherein M is a cation, a is the valence of M and is 1, 2 or 3; when a is 1, x is 2 and y is also 1; when a is 2, both x and y are 1; and when a is 3, x is 2 and y is 3.

11. The process of claim 10 wherein the inorganic salt is Na₂SO₄, CaSO₄, K₂SO₄, (NH₄)₂SO₄, Na₂SO₃ or K₂SO₃.

12. The process of claim 4 wherein said inorganic salt is represented by one of the following formulae: $M^a{}_x(XO_3)_y$, $M^a{}_x(XO_2)_y$, $M^a{}_x(XO)_y$ and $M^a{}_x(XO_4)_y$, wherein M is a cation, a is the valence of M and is 1, 2 or 3, x is always 1 and y is the same integer as a.

13. The process of claim 12 wherein the inorganic salt is KBrO₃, NaClO.H₂O, Ca(ClO)₂, NaClO₃, KClO, NaClO₄ or NaClO₂.

14. The process of claim 4 wherein the inorganic salt is waterglass of the formula (Na₂O).x SiO₂ wherein x is 3 to 5 or a water-soluble salt of one of the following silicic acids: H₂Si₄O₉, H₂Si₂O₅, H₄SiO₃O₈, H₂SiO₃, H₈Si₃O₁₀, H₆Si₂O₇ or H₄SiO₄.

15. The process of claim 14 wherein the inorganic salt is sodium metasilicate or sodium orthosilicate.

16. The process of claim 4 wherein the inorganic salt is represented by one of the following formulae:

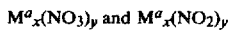
$M^a{}_x(NO_3)_y$ and $M^a{}_x(NO_2)_y$ wherein M is a cation, a is the valence of M and is 1, 2 or 3, y is the same integer as a, and x is always the integer 1.

17. The process of claim 16 wherein the inorganic salt is KNO₃, NaNO₂, Ca(NO₃)₂, NaNO₃, NH₄NO₃, KNO₂ or NH₄NO₂.

18. The process of claim 14 wherein the inorganic salt is waterglass of the formula (Na₂O).xSiO₂ wherein x is 3 to 5.

* * * * *